US010932696B2

United States Patent
De Vries et al.

(10) Patent No.: US 10,932,696 B2
(45) Date of Patent: Mar. 2, 2021

(54) DETERMINING A MEASURE OF THE PHYSICAL FITNESS OF A SUBJECT

(71) Applicant: KONINKLIJKE PHILIPS N.V., Eindhoven (NL)

(72) Inventors: Jan Johannes Gerardus De Vries, Leende (NL); Dieter Maria Alfons Van De Craen, Balen (BE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 60 days.

(21) Appl. No.: 16/337,449

(22) PCT Filed: Sep. 29, 2017

(86) PCT No.: PCT/EP2017/074854
§ 371 (c)(1),
(2) Date: Mar. 28, 2019

(87) PCT Pub. No.: WO2018/060467
PCT Pub. Date: Apr. 5, 2018

(65) Prior Publication Data
US 2019/0343428 A1   Nov. 14, 2019

(30) Foreign Application Priority Data
Sep. 30, 2016  (EP) ................................ 16191759

(51) Int. Cl.
*A61B 5/11*  (2006.01)
*A61B 5/22*  (2006.01)
*A61B 5/00*  (2006.01)

(52) U.S. Cl.
CPC ............ *A61B 5/1116* (2013.01); *A61B 5/225* (2013.01); *A61B 5/6891* (2013.01);
(Continued)

(58) Field of Classification Search
CPC ................ A61B 5/00; G01F 1/34; A61H 1/02
See application file for complete search history.

(56) References Cited

U.S. PATENT DOCUMENTS 5,078,152 A * 1/1992 Bond ................... G06F 19/3481
                                                    600/587
5,403,251 A * 4/1995 Belsito .................... A63B 24/00
                                                    482/4
(Continued)

FOREIGN PATENT DOCUMENTS

GB       2503413 A      1/2014
TW    201208647 A      3/2012
(Continued)

OTHER PUBLICATIONS

Arcelus, A. et al., "Measurements of Sit-to-Stand Timing and Symmetry From Bed Pressure Sensors", IEEE Transactions on Instrumentation and Measurement, IEEE Service Center, vol. 60, No. 5, May 2011.
(Continued)

*Primary Examiner* — Harshad R Patel (57) ABSTRACT

According to an aspect there is provided an apparatus for determining a measure of the physical fitness of a subject, the apparatus comprising a processing unit that is configured to receive a first measurement signal from a first sensor that measures the force or pressure exerted on an object by the subject over time, the first measurement signal comprising measurements representing the force or pressure exerted on the object during a first movement in which the subject sits down on the object and/or during a second movement in which the subject stands up after sitting on the object; and analyze the first measurement signal to determine the measure of the physical fitness of the subject.

12 Claims, 7 Drawing Sheets

(52) U.S. Cl.
CPC ........ *A61B 5/7278* (2013.01); *A61B 2503/08* (2013.01); *A61B 2562/0219* (2013.01); *A61B 2562/0247* (2013.01)

(56) References Cited

U.S. PATENT DOCUMENTS

| | | | | |
|---|---|---|---|---|
| 5,417,643 | A * | 5/1995 | Taylor | A61H 1/0274 601/24 |
| 5,618,250 | A * | 4/1997 | Butz | A63B 21/0615 482/134 |
| 5,843,004 | A * | 12/1998 | Presl | A63B 21/00178 600/595 |
| 6,672,157 | B2 * | 1/2004 | MacFarlane | A61B 5/224 73/379.01 |
| 6,695,795 | B2 * | 2/2004 | Knoll | A61H 1/0281 601/26 |
| 7,412,904 | B2 * | 8/2008 | Holder | A61B 5/224 73/861.42 |
| 10,118,073 | B2 * | 11/2018 | Wicks | A63B 21/023 |
| 2004/0260156 | A1 * | 12/2004 | David | A61B 5/04085 600/300 |
| 2013/0110475 | A1 | 5/2013 | Greene et al. | |
| 2015/0272511 | A1 | 10/2015 | Najafi et al. | |
| 2015/0305656 | A1 | 10/2015 | Takehara et al. | |
| 2015/0374281 | A1 * | 12/2015 | Breuille | A61B 5/4884 600/595 |

FOREIGN PATENT DOCUMENTS

| | | |
|---|---|---|
| WO | 2013056218 A2 | 4/2013 |
| WO | 2016075175 A1 | 5/2016 |

OTHER PUBLICATIONS

Munro, B. et al., "A kinematic and kinetic analysis of the sit-to-stand transfer using an ejector chair: implications for elderly rheumatoid arthritic patients", Journal of Biomechanics, 31, 1998.

Knight, H. et al., "Chair Alarm for Patient Fail Prevention based on Gesture Recognition and Interactivity", 30th Annual International IEEE EMBS Conference, Canada, Aug. 2008.

Mourey, F. et al., "A kinematic comparison between elderly and young subjects standing up from and sitting down in a chair", Age and Aging, 1998, 27, 137-146.

"Groningen Frailty Indicator", http://www.platformouderenzorg.nl/, Accessed Mar. 26, 2019.

* cited by examiner

DETERMINING A MEASURE OF THE PHYSICAL FITNESS OF A SUBJECT

This application is the U.S. National Phase application under 35 U.S.C. § 371 of International Application No. PCT/EP2017/074854, filed on 29 Sep. 2017, which claims the benefit of European Application Serial No. 16191759.6, filed 30 Sep. 2016. These applications are hereby incorporated by reference herein.

TECHNICAL FIELD OF THE INVENTION

This disclosure relates to determining a measure of the physical fitness of a subject, and in particular to an apparatus and method for determining a measure of the physical fitness from a movement in which the subject sits down on an object and/or a movement in which the subject stands up after sitting on the object.

BACKGROUND OF THE INVENTION

People experience degradation of their physical fitness and motoric skills as they age. The process can be very gradual and is therefore not easily observed by the person themselves, their family members, or caregivers. As motoric skills deteriorate, it becomes increasingly difficult to perform normal everyday activities such as dressing and bathing, and as a result, a person may begin to lose their ability to live independently, therefore requiring higher levels of care. As the person's condition deteriorates, lower gross motoric skills lead to generally reduced mobility and balance which increases the person's chances of falling. Given the already frail health status of elderly people, fall incidents can have a significant negative impact on health and quality of life. Falls can also result in increased care costs due to the resulting injuries, hospitalizations and home-based care requirements as the person recovers.

Because of the high costs involved in higher levels of care, it is of high interest to detect a reduction in motoric skills early on so that support can be provided as soon as it is needed to enable the person to live safely and independently for as long as possible.

A reduction in physical fitness, for example, a reduction in motoric skills, can be an indicator of the frailty of an elderly person. Frailty can be subdivided into a component that reflects fine motoric skills, for example, the ability to perform small movements of the wrists, hands, fingers, feet and toes, etc. and a component that reflects gross motoric skills, for example, the strength in the person's arms and legs.

Motoric skills, or more generally physical fitness, are typically measured by having the person perform certain tasks, which are assessed by a nurse or clinician. One such task is to stand up and sit down again repeatedly. A nurse or clinician times the action and uses the time taken as an indicator of the person's physical fitness. This is a subjective measurement, however, and is difficult to use to determine gradual changes in motoric skills.

In a more controlled environment such as a research environment, there are systems that measure motoric skills using a camera system or a multitude of accelerometers to determine the detailed movements of the person's limbs. These methods are time consuming, costly and require the person to visit a clinical environment. As a consequence, such tests are often performed sparsely and thus a reduction in motoric skill can be detected late, leading to higher care costs than would otherwise be necessary.

It is an object of the present disclosure to provide an improved way of measuring the physical fitness of a subject.

SUMMARY OF THE INVENTION

According to a first aspect there is provided an apparatus for determining a measure of the physical fitness of a subject, the apparatus comprising a processing unit that is configured to receive a first measurement signal from a first sensor that measures the force or pressure exerted on an object by the subject over time, the first measurement signal comprising measurements representing the force or pressure exerted on the object during a first movement in which the subject sits down on the object and/or during a second movement in which the subject stands up after sitting on the object; and analyze the first measurement signal to determine the measure of the physical fitness of the subject. This aspect therefore provides an apparatus that can determine a measure of the physical fitness of the subject unobtrusively and accurately from a movement that is typically performed by the subject several times a day.

In some embodiments, the processing unit is configured to analyze one or more characteristics of a profile formed from the first measurement signal to determine the measure of the physical fitness.

The one or more characteristics can comprise a measure based on the local maxima and/or minima in the profile or in a part of the profile. This characteristic provides an indication of the smoothness of the first and/or second movement by the subject. The one or more characteristics can also or alternatively comprise a measure based on the derivative with respect to time of the profile. This characteristic provides an indication of how quickly the subject performed the first and/or second movement. The one or more characteristics can also or alternatively comprise the maximum magnitude of the first measurement signal. This characteristic can also provide an indication of how quickly the subject performed the first and/or second movement. In some embodiments, the processing unit is configured to analyze the first measurement signal to determine a start time and an end time of the first movement and/or the second movement, and the one or more characteristics comprises the time between the determined start time and end time. The one or more characteristics can also or alternatively comprise a measure of the variation of a derivative with respect to time of the profile or part of the profile. This characteristic provides an indication of how smoothly the subject performed the first and/or second movement.

In some embodiments, the first measurement signal comprises measurements representing the force or pressure exerted on a part of the object on which the subject sits; and the processing unit is further configured to receive a second measurement signal from a second sensor that measures a second force or pressure exerted on an arm rest of the object that can be used by the subject during the first movement and/or during the second movement, the second measurement signal comprising measurements representing the force or pressure exerted on the arm rest during the first movement and/or during the second movement; and wherein the processing unit is configured to analyze the first and second measurement signals to determine the measure of the physical fitness of the subject. This embodiment provides information on how the subject uses their hands or arms to assist them in completing the movement. In some embodiments, the apparatus further comprises the second sensor. In some embodiments, the second sensor is one of a pressure sensor, a force sensor and a sensor for measuring the skin conductance of the subject. These sensors can be used to unobtrusively obtain the measurements.

In some embodiments, the apparatus is further configured to determine the grip strength of the subject by analyzing the first measurement signal and the second measurement signal. Grip strength is a useful measure of the physical fitness of a subject.

The first sensor can be a pressure sensor, a force sensor or a sensor that measures the speed of air flow. These sensors can be used to unobtrusively obtain the measurements. In some embodiments, the first sensor can measure at least one of the speed of air flowing into the object during the second movement; the speed of air flowing out of the object during the first movement; and the speed of air flowing between two or more internal portions of the object during the first movement and/or during the second movement.

In some embodiments, the first sensor is located on a part of the object on which the subject sits.

According to a second aspect, there is provided a method of determining a measure of physical fitness of a subject, the method comprising receiving a first measurement signal from a first sensor that measures the force or pressure exerted on an object by the subject over time, the first measurement signal comprising measurements representing the force or pressure exerted on the object during a first movement in which the subject sits down on the object and/or during a second movement in which the subject stands up after sitting on the object; and analyzing the first measurement signal to determine the measure of the physical fitness of the subject.

In some embodiments, the step of analyzing comprises analyzing one or more characteristics of a profile formed from the first measurement signal to determine the measure of the physical fitness.

The one or more characteristics can comprise a measure based on the local maxima and/or minima in the profile or in a part of the profile. This characteristic provides an indication of the smoothness of the first and/or second movement by the subject. The one or more characteristics can also or alternatively comprise a measure based on the derivative with respect to time of the profile. This characteristic provides an indication of how quickly the subject performed the first and/or second movement. The one or more characteristics can also or alternatively comprise the maximum magnitude of the first measurement signal. This characteristic can also provide an indication of how quickly the subject performed the first and/or second movement. In some embodiments, the step of analyzing comprises analyzing the first measurement signal to determine a start time and an end time of the first movement and/or the second movement, and the one or more characteristics comprises the time between the determined start time and end time. The one or more characteristics can also or alternatively comprise a measure of the variation of a derivative with respect to time of the profile or part of the profile. This characteristic provides an indication of how smoothly the subject performed the first and/or second movement.

In some embodiments, the first measurement signal comprises measurements representing the force or pressure exerted on a part of the object on which the subject sits; and the method further comprises receiving a second measurement signal from a second sensor that measures a second force or pressure exerted on an arm rest of the object that can be used by the subject during the first movement and/or during the second movement, the second measurement signal comprising measurements representing the force or pressure exerted on the arm rest during the first and/or second movement; and the step of analyzing comprises analyzing the first and second measurement signals to determine the measure of the physical fitness of the subject. This embodiment provides information on how the subject uses their hands or arms to assist them in completing the first and/or second movement. In some embodiments, the second sensor is one of a pressure sensor, a force sensor and a sensor for measuring the skin conductance of the subject. These sensors can be used to unobtrusively obtain the measurements.

In some embodiments, the step of analyzing further comprises determining the grip strength of the subject by analyzing the first measurement signal and the second measurement signal. Grip strength is a useful measure of the physical fitness of a subject.

The first sensor can be a pressure sensor, a force sensor or a sensor that measures the speed of air flow. These sensors can be used to unobtrusively obtain the measurements. In some embodiments, the first sensor can measure at least one of the speed of air flowing into the object during the second movement; the speed of air flowing out of the object during the first movement; and the speed of air flowing between two or more internal portions of the object during the first movement and/or during the second movement.

In some embodiments, the first sensor is located on a part of the object on which the subject sits.

According to a third aspect, there is provided a computer program product comprising a computer readable medium having computer readable code embodied therein, the computer readable code being configured such that, on execution by a suitable computer or processor, the computer or processor is caused to perform any of the methods described above.

In the third aspect, the computer readable code can be configured such that, on execution by a suitable computer or processor, the computer or processor is caused to receive a first measurement signal from a first sensor that measures the force or pressure exerted on an object by the subject over time, the first measurement signal comprising measurements representing the force or pressure exerted on the object during a first movement in which the subject sits down on the object and/or during a second movement in which the subject stands up after sitting on the object; and analyze the measurements representing the force or pressure to determine the measure of the physical fitness of the subject.

The computer program product comprises a computer-readable storage medium having computer-readable program code embodied therewith, the computer-readable program code being configured to perform all of the steps of an embodiment.

In an embodiment, a computer system may be provided which comprises: a computer program product according to an embodiment; and one or more processors adapted to perform a method according to an embodiment by execution of the computer-readable program code of said computer program product.

In a further aspect the invention relates to a computer-readable non-transitory storage medium comprising instructions which, when executed by a processing device, execute the steps of the method according to any of the above embodiments.

According to a fourth aspect, there is provided an apparatus for determining a measure of the physical fitness of a subject, the apparatus comprising a processing unit that is configured to: receive a first measurement signal from a first sensor that measures the force or pressure exerted on an object by the subject over time, the first measurement signal comprising measurements representing the force or pressure exerted on a part of the object on which the subject sits during a first movement in which the subject sits down on the object and/or during a second movement in which the subject stands up after sitting on the object; receive a second measurement signal from a second sensor that measures a second force or pressure exerted on an arm rest that can be used by the subject during the first movement and/or during the second movement, the second measurement signal comprising measurements representing the force or pressure exerted on the arm rest during the first movement and/or during the second movement; analyze the first and second measurement signals to determine the measure of the physical fitness of the subject; wherein the measure of the physical fitness is the grip strength of the subject.

In some embodiments, the processing unit is configured to determine the grip strength by subtracting a force due to the weight of the subject determined from the first measurement signal from a force exerted on the arm rest determined from the second measurement signal.

In some embodiments, the force due to the weight of the subject is measured by the first sensor when the subject is fully sitting.

In some embodiments, the processing unit is configured to determine the grip strength by: subtracting the force of the weight of the subject f_s_max, from each measurement in the second measurement signal, f_r to obtain f_r−f_s_max; and calculating the grip strength by summing the values of f_r−f_s_max for which f_r−f_s_max>0.

In some embodiments, the processing unit is further configured to analyze one or more characteristics of a profile formed from the first measurement signal to determine another measure of the physical fitness of the subject.

In some embodiments, the one or more characteristics comprises a measure based on the local maxima and/or minima in the profile or in a part of the profile.

In some embodiments, the one or more characteristics comprises a measure based on the derivative with respect to time of the profile.

In some embodiments, one or more characteristics comprises the maximum magnitude of the first measurement signal.

In some embodiments, the processing unit is configured to analyze the first measurement signal to determine a start time and an end time of the first movement and/or the second movement, and wherein the one or more characteristics comprises the time between the determined start time and end time.

In some embodiments, the one or more characteristics comprises a measure of the variation of a derivative with respect to time of the profile or part of the profile.

In some embodiments, the first sensor is a pressure sensor, a force sensor or an airflow sensor.

According to a fifth aspect, there is provided a method of determining a measure of physical fitness of a subject, the method comprising receiving a first measurement signal from a first sensor that measures the force or pressure exerted on an object by the subject over time, the first measurement signal comprising measurements representing the force or pressure exerted on a part of the object on which the subject sits during a first movement in which the subject sits down on the object and/or during a second movement in which the subject stands up after sitting on the object; receiving a second measurement signal from a second sensor that measures a second force or pressure exerted on an arm rest that can be used by the subject during the first movement and/or during the second movement, the second measurement signal comprising measurements representing the force or pressure exerted on the arm rest during the first movement and/or during the second movement; analyzing the first and second measurement signal to determine the measure of the physical fitness of the subject; wherein the measure of the physical fitness is the grip strength of the subject.

In some embodiments, the step of analyzing further comprises analyzing one or more characteristics of a profile formed from the first measurement signal to determine another measure of the physical fitness of the subject.

In some embodiments, the one or more characteristics comprises any one or more of (i) a measure based on the local maxima and/or minima in the profile or in a part of the profile; (ii) a measure based on the derivative with respect to time of the profile; (iii) the maximum magnitude of the first measurement signal; (iv) the time between a start time and end time of the first movement and/or the second movement; and (v) a measure of the variation of a derivative with respect to time of the profile or part of the profile.

According to a sixth aspect, there is provided a computer program product comprising a computer readable medium having computer readable code embodied therein, the computer readable code being configured such that, on execution by a suitable computer or processor, the computer or processor is caused to perform any of the methods according to the fifth aspect.

BRIEF DESCRIPTION OF THE DRAWINGS

Exemplary embodiments of the invention will now be described, by way of example only, with reference to the following drawings, in which.

DETAILED DESCRIPTION OF THE EMBODIMENTS

As described above, it is often difficult to measure changes in physical fitness of a person (such as changes in motoric skills and/or frailty) over time, since the changes are often gradual and many methods of determining levels of physical fitness require the presence of a caregiver.

One way to assess the physical fitness is to observe a stand to sit movement and/or a sit to stand movement made by the subject to provide an indicator of physical fitness. In particular, sit to stand and stand to sit movements are typically smooth and well controlled in subjects with high levels of physical fitness as these subjects are able to lower themselves down into, or up from a seated position on a chair in a controlled manner. Conversely, such movements may be jerky or characterized by tremors for less fit subjects if the subject struggles to support their weight as they move from standing to sitting (or vice versa). In more frail subjects still, the subject may not be able to control a stand to sit movement at all and may 'slump' into the chair under gravity. Thus, how a subject sits down or stands up can be used as a measure of physical fitness.

As noted above, a subject's movements can be assessed using a camera system or a multitude of accelerometers to determine the detailed movements of the subject's limbs. However, this type of measurement system is not that convenient for a subject to use, particularly in their own home.

Thus, it has been appreciated that in cases where the subject sits down on or stands up from an object (for example a chair or bed), the pressure or force exerted on the object as the person makes the movement can be used to assess the movement and thus provide a measure of the physical fitness.

Embodiments described herein thus provide an improved method and apparatus for determining a measure of the physical fitness of the subject that uses measurements of a movement in which the subject sits down on an object and/or a movement in which the subject stands up after sitting on the object. The apparatus comprises a processing unit that receives a first measurement signal from a first sensor that measures the force or pressure exerted on an object by a subject over time. The first measurement signal comprises measurements representing the force or pressure exerted on the object during a movement in which the subject sits down on the object and/or during a movement in which the subject stands up after sitting on the object. The measurements representing the force or the pressure are then analyzed to determine the measure of the physical fitness of the subject. Thus the measure of the physical fitness can be obtained from an everyday movement.

Furthermore, in some embodiments the first sensor can be in, on or part of an object, such as a chair or a bed which means that the measurements can be obtained unobtrusively. The embodiments herein thus provide a cost-effective way of regularly measuring the physical fitness of a subject, for example, in the subject's home, without the need for measurements to be made in a clinical setting.

Figure 1:
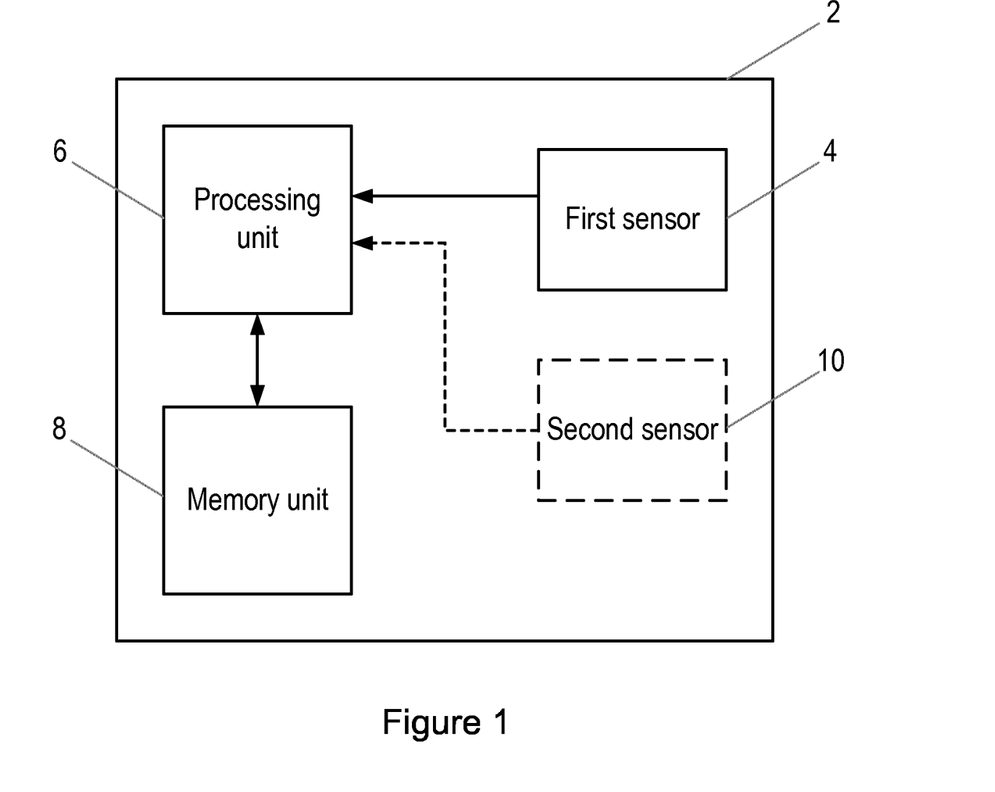
FIG. 1 is a block diagram of an apparatus according to an embodiment.

An embodiment of an apparatus 2 for determining a measure of the physical fitness of a subject is shown in FIG. 1. The apparatus 2 comprises a first sensor 4 that measures the force or pressure exerted on an object by the subject over time. The object can be any object that can bear the weight of a subject, such as a chair, sofa, stool or bed, or a mattress or cushion for any of those objects.

The first sensor 4 may directly measure the force or pressure, for example, the first sensor 4 may include a piezoelectric sensor, a capacitive sensor, an electromagnetic sensor, or an optical sensor to measure the strain on or deflection of an element of the first sensor 4 due to the applied force, or the first sensor 4 may be a force sensor that measures the weight being exerted on the object.

In alternative embodiments, the first sensor 4 can indirectly measure the force or pressure. For example, if a portion of the object ordinarily contains air that is displaced or forced out of the object when compressed (for example a cushion), then the speed of air flowing within or out of the object as the subject sits down on the object will be related to the force or pressure applied on the object by the subject, and thus measurements of the air flow speed can be used in place of direct measurements of force or pressure. Similarly, if the object is such that air is drawn into the object when force is removed from the object (for example, re-inflation of a cushion from a compressed state when a person gets up from having sat on it) then the first sensor 4 can be an airflow sensor that measures the speed of air flowing into the object as the subject stands up from having sat on the object.

The skilled person will be aware of different types of airflow sensor that can be used for this purpose, such as a sensor comprising a rotor that will rotate in one or the other direction given air flowing from one or the other direction, with the speed of rotation being proportional to the speed with which air is flowing through the sensor, or a sensor based on measurements of the amount of heat dissipating from a probe over which the air flows (with the amount of heat dissipation being proportional to the speed with which air is flowing over the probe). The airflow sensor is preferably able to detect air flow bi-directionally, so as to measure force or pressure during both a sit down and stand up movement. The output of the airflow sensor can be a signal representing measurements of flow rate (e.g. in liters per second (L/s)) measured at various moments in time.

In addition to the example sensor types above, those skilled in the art will be aware of other types of pressure or force sensor that can be used in an apparatus 2 to measure the force or pressure exerted by a subject on the object.

In some embodiments, the first sensor 4 is integrated into the object, for example, the first sensor 4 may be embedded within a part of the object that is to be sat on, for example, the seat portion of a chair, a cushion or a mattress for a bed. In other embodiments, the first sensor 4 is separate from the object, for example, the first sensor 4 can be in a pad that can be placed over the surface of the object, or the first sensor can be part of a device that can be worn by the person and arranged to measure the force or pressure on the object as the subject sits down or stands up.

A measurement signal representing the force or pressure exerted on the object is provided from the first sensor 4 to a processing unit 6 in the apparatus 2. The processing unit 6 processes the measurement signal to determine the measure of the physical fitness of the subject, as described in more detail below.

The processing unit 6 can also control the operation of the apparatus 2, for example controlling the initiation of the collection of measurements by the first sensor 4, and/or other functions and operations of the apparatus 2. The processing unit 6 can be implemented in numerous ways, with software and/or hardware, to perform the various functions required. The processing unit 6 may comprise one or more microprocessors that may be programmed using software to perform the required functions. The processing unit 6 may be implemented as a combination of dedicated hardware to perform some functions and a processor (e.g., one or more programmed microprocessors and associated circuitry) to perform other functions. Examples of processing components that may be employed in various embodiments of the present disclosure include, but are not limited to, conventional microprocessors, application specific integrated circuits (ASICs), and field-programmable gate arrays (FPGAs).

In various implementations, the processing unit 6 may be associated with one or more storage media, shown as memory unit 8 in FIG. 1. The memory unit 8 can be part of the processing unit 6, or it can be a separate component in the apparatus 2 that is connected to the processing unit 6 (as shown in FIG. 1). The memory unit 8 can comprise any suitable or desired type of volatile or non-volatile computer memory such as RAM, PROM, EPROM, and EEPROM. The memory unit 8 can be used for storing computer program code that can be executed by the processing unit 6 to perform the method described herein. The memory unit 8 can also be used to store signals or measurements from the first sensor 4 and/or any other sensors in the apparatus 2, and/or information relating to the measure of physical fitness determined by the processing unit 6.

In some embodiments, all of the components of the apparatus 2 are part of the same device, e.g. the first sensor 4 and processing unit 6 are in a single housing. In other embodiments the first sensor 4 is in a separate device or housing to the processing unit 6. Where the first sensor 4 is provided in a separate device or housing to the processing unit 6, appropriate circuitry or components can be provided to enable the measurement signal to be sent (e.g. transmitted) to the processing unit 6. In these cases the processing unit 6 can be part of a personal electronic device such as a smartphone, tablet computer, laptop computer or desktop computer, or part of another electronic device, such as a base unit or hub unit for the first sensor 4, or a remote server (e.g. located in the cloud, i.e. accessible via the Internet), in which case the measurements from the first sensor 4 can be sent wirelessly to the processing unit 6 in the electronic device using any suitable communication protocol (e.g. Wi-Fi, Bluetooth, or a cellular telecommunication protocol) so that the measure of physical fitness can be determined.

In some embodiments the processing unit 6 can receive the measurement signal from the first sensor 4 in real-time or near real-time (e.g. with the only delay being due to the signal processing required to transmit or convey the measurements to the processing unit 6. In other embodiments (including embodiments where the first sensor 4 is separate from the processing unit 6, the measurements from the first sensor 4 can be stored in memory unit 8 and the processing unit 6 can retrieve and analyze the previously-obtained measurements from the memory unit 8 when a measure of physical fitness is to be determined.

As noted above, in some embodiments the processing unit 6 may be part of a smartphone or other general purpose computing device that can be connected to or otherwise receive a measurement signal from first sensor 4, but in other embodiments the apparatus 2 can be an apparatus that is dedicated to the purpose of determining the measure of physical fitness of a subject.

In some embodiments, the apparatus 2 further comprises a second sensor 10. The second sensor 10 is provided to measure the force or pressure exerted on another part of object by the subject over time. In embodiments where the first sensor 4 is located on a part of the object in which the subject sits (e.g. a cushion or a base for a chair), the second sensor 10 may be located on an arm rest of the object that subject can sit on (e.g. an arm rest of the chair) or an arm rest of another object (e.g. the arm rest can be a walking frame, a hand rail, etc.). The arm rest of the object or the arm rest of the other object may be any part of the or other object that the subject can grip or push against with their hand or arm in order to support their weight or for balance during the movement in which the subject sits down on the object and/or during the movement in which the subject stands up after sitting on the object. It will be appreciated that where the object is a bed, the arm rest may correspond to a bed rail or a rail mounted to the wall or other object. In other embodiments the arm rest can be a handle or similar. The second sensor 10 can therefore provide a second measurement signal that represents the force or pressure exerted on the arm rest, and the processing unit 6 may analyze both the first and second measurement signals to determine the measure of the physical fitness of the subject, as will be described in more detail below. In some embodiments, the processing unit 6 may process the second measurement signal to obtain a measure of the grip strength of the subject. In other words, in these embodiments the measure of the physical fitness can be the grip strength of the subject. In embodiments where the object is a chair or similar having two arm rests (i.e. one for each arm), respective second sensors 10 can be provided on each arm rest of the object (or arm rest of the other object, such as a walking frame), and the measurement signals from each second sensor 10 can be analyzed by the processing unit 6 to determine the measure of the physical fitness of the subject (e.g. measurements of grip strength for each hand).

The second sensor 10 can be a pressure or force sensor (e.g. similar to the first sensor 4) or a sensor that indirectly measures force or pressure through, for example, a resistive measurement, since a skin conductance measurement is highly influenced by the pressure or force applied to the electrodes. Thus in some embodiments the second sensor 10 is a skin conductance sensor.

It will be appreciated that FIG. 1 only shows the components required to illustrate various embodiments of the apparatus 2, and in a practical implementation the apparatus 2 may comprise additional components to those shown. For example, the apparatus 2 may comprise a battery or other power supply for powering the apparatus 2, a communication module for enabling the information on a determined measure of the physical fitness of a subject to be communicated to another device, e.g. a base unit for the apparatus 2 or a remote computer. As an example, the one or more user interface components could comprise a switch, a button or other control means for activating and deactivating the apparatus 2 and/or physical fitness determination process, although in a preferred embodiment, no interaction between the subject and apparatus is required to determine the measure of physical fitness. The user interface components can also or alternatively comprise a display or other visual indicator for providing information to the subject and/or other user about the operation of the apparatus 2, including displaying information on a determined measure of physical fitness, and/or information to educate the subject about exercises, activities or tasks to perform or avoid in order to improve their physical fitness.

Figure 2:
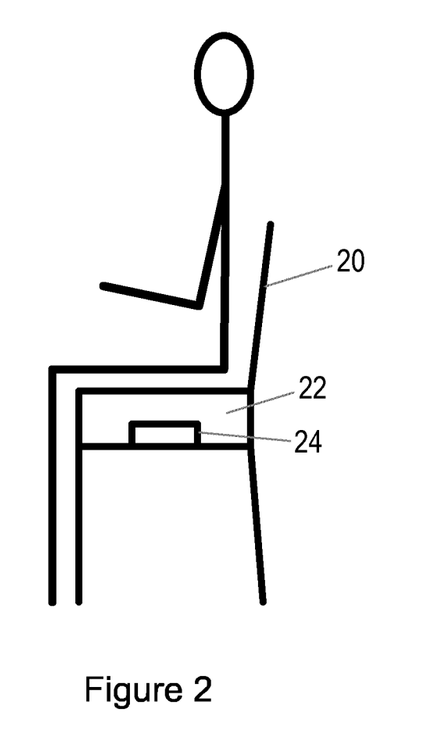
FIG. 2 is a diagram of an apparatus according to an embodiment.

An example apparatus 2 according to the invention in use with an object in the form of a chair is shown in FIG. 2. Thus FIG. 2 shows a chair 20 comprising a cushion 22. In this example, the first sensor 4, in the form of a force or pressure sensor 24, is positioned between the frame of the chair 20 and the cushion 22. The force or pressure sensor 24 measures the force or pressure exerted on the chair 20 as a subject 26 sits on the cushion 22 and chair 20. In an alternative example, the force or pressure sensor 24 can be part of the cushion 22.

Figure 3:
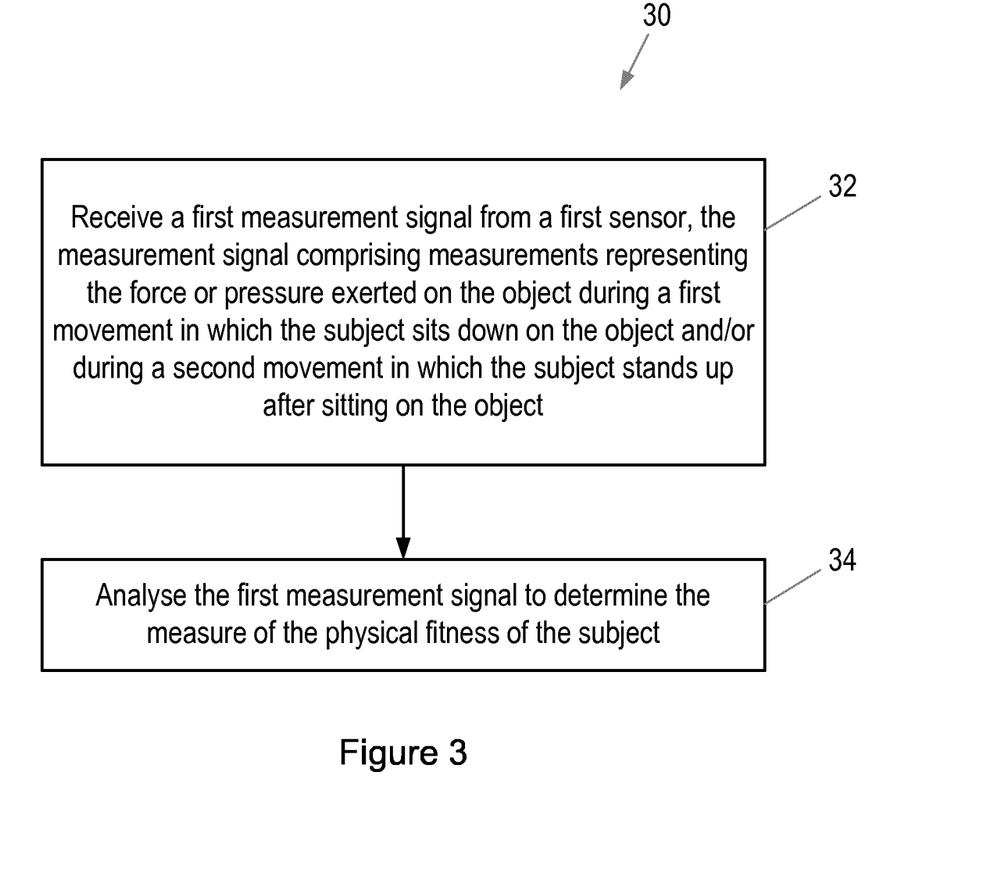
FIG. 3 is a flow chart illustrating a general method of determining a measure of the physical fitness of a subject.

The flow chart in FIG. 3 illustrates a general method of determining a fall risk according to an embodiment. The method can be performed by processing unit 6.

In a first step, a first measurement signal from a first sensor 4 that measures the force or pressure exerted on an object by the subject over time is received (step 32). The first measurement signal comprises measurements representing the force or pressure exerted on the object during a movement in which the subject sits down on the object (which is also referred to as the 'first' movement herein) and/or during a movement in which the subject stands up after sitting on the object (which is also referred to as the 'second' movement herein). The first measurement signal can be received directly from the first sensor 4, or the first measurement signal can be retrieved from a memory unit 8. The former case is useful where the measure of physical fitness is to be determined in real-time or near real-time. The first measurement signal may comprise measurements of force or pressure, measurements that represent the force or pressure (e.g. measurements of air flow by an air flow sensor) or other measurements that have been processed or converted into measurements representing force or pressure (for example air flow measurements that have been integrated with respect to time to provide a pressure or force signal). In some embodiments, the measurements may be filtered, e.g. to remove noise.

In a second step, the measurements representing the force or pressure (the first measurement signal) are analyzed to determine the measure of the physical fitness of the subject (step 34). The measure can comprise any type of information that can represent or indicate the physical fitness of the subject, for example a numerical score (that, for example, indicates the level of physical fitness of the subject relative to a defined scale), a binary indication (e.g. representing fit, not fit), a measure in the form of words (e.g. fit/not fit), etc.

Embodiments of step 34 are described in more detail below with reference to FIG. 4 that shows three exemplary measurement signals for stand to sit movements made by subjects with three different levels of physical fitness and FIG. 5 that shows three exemplary measurement signals for sit to stand movements made by subjects with three different levels of physical fitness.

Figure 4:
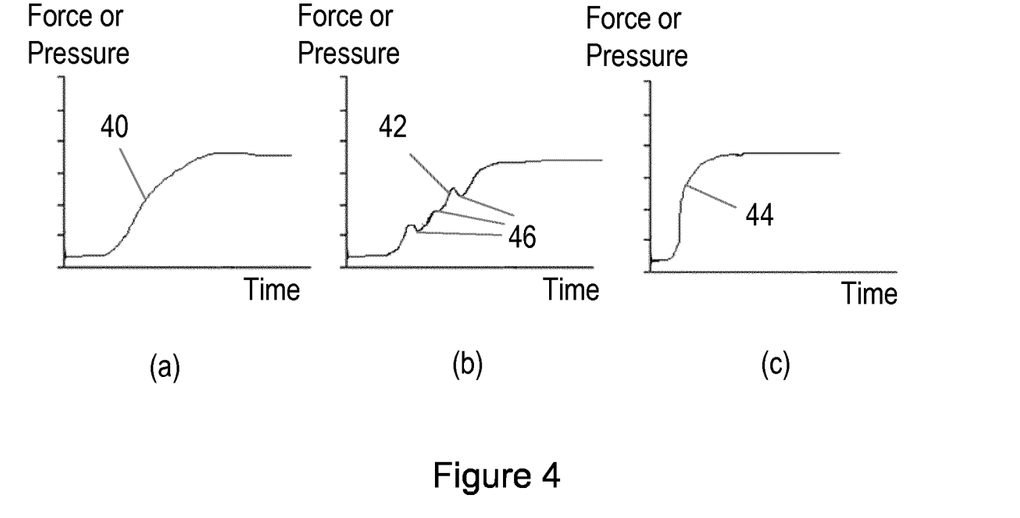
FIG. 4 is a set of graphs showing three profiles of the force/pressure on an object during a movement in which the subject sits down on the object.

FIG. 4(*a*) shows the measurements obtained for a subject with a high level of physical fitness (i.e. a 'healthy' or 'non-frail' profile). It can be seen that a profile or curve formed from the measurements relatively smoothly increases from a low level (where the subject first comes into contact with the first sensor 4) to a high level (where the subject has finished the movement and is sitting on the object). The profile or curve is relatively smooth because the subject is able to lower themselves onto the object with a high degree of control without 'slumping' (i.e. just dropping their weight) on to the object.

FIG. 4(*b*) shows the measurements obtained for a subject with a lower level of physical fitness, and it can be seen that the descent on to the object is not smooth, with some jerky movements resulting in small oscillations 42 in the profile, which indicates that the subject has a lower degree of control over their movements.

FIG. 4(*c*) shows the measurements obtained for a subject that has a low level of physical fitness (e.g. a frail subject). It can be seen that although the profile of the measurements is relatively smooth (similar to FIG. 4(*a*)), the gradient of the profile in the descent stage is much steeper indicating that the subject has 'slumped' down onto the object, perhaps because they cannot support their own weight properly with their arms and legs.

Figure 5:
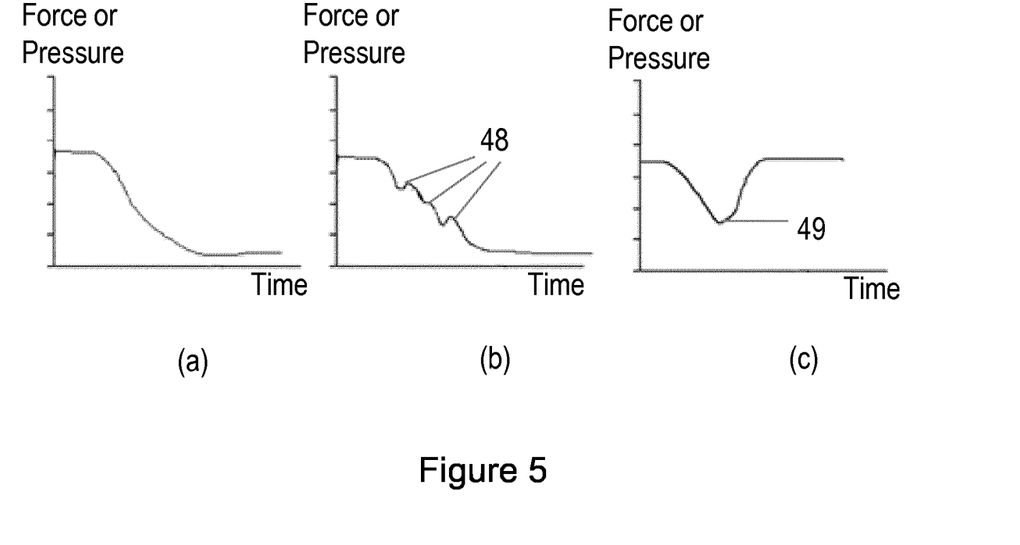
FIG. 5 is a set of graphs showing three profiles of the force/pressure on an object during a movement in which the subject stands up from sitting on the object.

FIG. 5(*a*) shows the measurements obtained for a subject with a high level of physical fitness (i.e. a 'healthy' or 'non-frail' profile). It can be seen that a profile or curve formed from the measurements relatively smoothly decreases from a high level (where the subject is fully sitting on the object) to a low level (where the subject has got up from the object and is no longer exerting any force or pressure on the object). The profile or curve is relatively smooth because the subject is able to lift themselves off of the object with a high degree of control.

FIG. 5(*b*) shows the measurements obtained for a subject with a lower level of physical fitness, and it can be seen that the ascent (i.e. getting up) from the object is not smooth, with some jerky movements resulting in small oscillations 48 in the profile, which indicates that the subject has a lower degree of control over their movements.

FIG. 5(*c*) shows the measurements obtained for a subject that has a low level of physical fitness (e.g. a frail subject). In this case, the subject tries to get up from the object (as shown by the profile being similar to that in FIG. 5(*a*)), but fails (e.g. because they lose their balance, or because they are not strong enough to lift their entire body weight) and sits back down on the object. This change in the direction of the movement is shown by minima 49.

In some embodiments, the step of analyzing 34 comprises analyzing one or more characteristics of a profile formed from the first measurement signal. In some embodiments, the first measurement signal may be filtered in order to remove or reduce noise in the measurements prior to determining the measure of the physical fitness.

The one or more characteristics can comprise a measure based on the local maxima and/or minima in the profile or a part of the profile. For example, the measure can be the number of local maxima and/or minima (minima are indicated by reference numeral 46 in FIG. 4(*b*) and numeral 49 in FIG. 5(*b*)) in the profile or in the part of the profile (e.g. a part corresponding to the descent on to the object or the ascent from the object). The number of local maxima and/or minima in the profile or the part of the profile is an indicator of the smoothness of the movement, and in general, the lower the number of local maxima and/or minima, the higher the level of physical fitness of the person. It will be appreciated that an equivalent measure to the number of local maxima and/or minima that can be used is the number of zero-crossings of the derivative with respect to time of the measurement signal. In an ideal case, for a subject that has a high level of physical fitness, there will not be any local maxima and minima in the part of the first measurement signal corresponding to the descent or ascent (as appropriate). Another measure based on the local maxima and/or minima in the profile or a part of the profile could be the amplitude of the oscillations (e.g. given by the magnitude of the difference between adjacent maxima and minima).

In some embodiments, the one or more characteristics can comprise the steepness (gradient) of a part of the force or pressure profile (e.g. a part corresponding to the descent on to the object or the ascent from the object) or the maximum steepness (gradient) of the force or pressure profile. For example, the characteristic may comprise the maximum derivative with respect to time of the profile. As shown from a comparison of FIGS. 4(*a*) to 4(*c*) or a comparison of FIGS. 5(*a*) to 5(*b*), the steepness of the profile is an indicator of how much control the subject has over their ascent from the object or descent on to the object, with a lower derivative or lower maximum derivative indicating better control over their movement (and therefore higher physical fitness) when sitting down, and a higher derivative or higher maximum derivative indicating better control or strength in their movement (and therefore higher physical fitness) when standing up. It will be appreciated by those skilled in the art that specific values of the derivative that may indicate higher or lower fitness can be determined by evaluation of a population of subjects with differing levels of physical fitness. It will also be appreciated that the derivative is dependent on the weight of the subject, and thus in some embodiments the derivative can be normalized based on the weight of the subject (as determined from the first measurement signal when the subject is sitting fully on the object).

In some embodiments, particularly where the first sensor 4 is an airflow sensor, step 34 can comprise determining the maximum magnitude of the first measurement signal and determining the measure of the physical fitness of the subject from the maximum magnitude. In general, the lower the maximum magnitude, the higher the level of physical fitness. For example, in the case of an airflow sensor, a frail subject may slump down on to the object which will cause a higher air flow rate than a fit subject sitting down gently, and thus the maximum magnitude for the fit subject will be lower than for an unfit (e.g. frail) subject.

In some embodiments, the one or more characteristics comprises the duration of the movement in which the subject sits down on the object and/or the movement in which the subject stands up after sitting on the object (as appropriate). It will be appreciated that step 34 can comprise determining a start time and an end time of the movement, and determining the duration from the determined times. As shown in FIGS. 4(a) and 4(c), the duration of the movement observable in the measurement signal is an indicator of how much control the subject has over their ascent from the object or descent on to the object. In particular, a short duration or a particularly long duration when sitting down is an indication of lower physical fitness, whereas a long duration when standing up is an indicator of lower physical fitness (and a short duration when standing up an indicator of higher physical fitness). Suitable values indicative of long and short durations (and therefore high/low fitness) can be determined through evaluation of a number of subjects with differing levels of physical fitness. For example in the case of a sitting down movement, a duration of 0.5 seconds or less can be indicative of a subject that is unfit.

As the first sensor 4 can only provide useful measurements when the subject is in contact with the first sensor 4/object, it will be appreciated that it may not be possible to determine the exact start time of the complete movement in the case of the subject sitting down on the object (since the subject is initially standing and not in contact with the first sensor 4), or the exact end time of the complete movement in the case of the subject standing up from the object (since the subject will leave contact with the first sensor 4/object before becoming fully upright). Thus, the duration can be the duration of the movement that is observable in the first measurement signal. That is, for a sitting down movement, the duration can be the time from the first indication in the measurement signal that the subject is in contact with the object (e.g. when the amplitude of the measurement signal first exceeds a threshold) to the time where the measured pressure or force is generally constant (indicating that the subject has sat down completely). It will be appreciated that in the case of the first sensor 4 being an airflow sensor, the duration can correspond to the time taken for the measured air flow to return to zero. For a standing up movement, the duration can be the time from the first deviation from a constant value (or the first deviation that exceeds a threshold value) to the time where the measured pressure or force is zero (indicating that the subject is not exerting any force or pressure on the object). In one example, a duration of the order of 0.5 seconds when sitting down can be indicative of a subject that has a lower level of physical fitness.

In some embodiments, the one or more characteristics may comprise a measure of the variation of a derivative with respect to time of the profile or part of the profile. The measure of variation could be, for example, the standard deviation of the derivative or the inter-quartile range of the derivative. This measure of variation provides a direct indicator of the variability or jerkiness of the movement which reflects the physical fitness of the subject. The lower the measure of variation (e.g. zero or close to zero) the smoother the curve, and thus the smoother the movement and the fitter the subject.

It will be appreciated that multiple ones of the above characteristics can be determined for a particular sit to stand or stand to sit movement, and those characteristics combined in order to determine the measure of physical fitness. In some embodiments, each characteristic can be evaluated against a respective scale or set of thresholds to determine a score or value for each characteristic. These scores or values can be combined (e.g. summed or averaged) to determine an overall physical fitness score or value. In some embodiments, the scores or values can be weighted before summing or averaging to determine the overall physical fitness score. The weighting may be based on the usefulness of the particular characteristic as an indicator of physical fitness. The typical scales or thresholds can be determined through evaluation of a population of subjects having different levels of physical fitness (e.g. as measured by conventional methods).

As an alternative, each of the determined characteristics can be evaluated against a single respective threshold to provide a binary indicator of physical fitness and then the findings of these evaluations combined to determine the overall measure of physical fitness. For example where each characteristic provides a binary indicator of fitness (e.g. fit/unfit), an overall physical fitness measure can be derived based on a simple majority, i.e. where more characteristics indicate that the subject is fit, the overall measure can be 'fit'. Alternatively, the binary indicators can be combined (e.g. summed) to determine a physical fitness score. In some embodiments, the binary indicators can be weighted before summing and averaging to determine a physical fitness score. As above, the weighting may be based on the usefulness of the particular characteristic as an indicator of physical fitness.

In general, a smooth curve (profile), for example as shown in FIG. 4(a), that has a relatively low maximum, a low number of maxima and/or minima in the profile, and has a 'medium' duration, corresponds to a subject with good motor skills and thus high levels of physical fitness. A more 'jerky' curve, for example as shown in FIG. 4(b), with a relatively low maximum, large numbers of maxima and minima, and of a long duration, corresponds to poor motor skills and thus lower levels of physical fitness. A 'quick' curve, for example as shown in FIG. 4(c), with a high maximum, a low number of zero crossings of the derivative with respect to time (low number of maxima and minima) and a short duration corresponds to a low level of physical fitness.

In some embodiments, the step of analyzing the measurements 34 can comprise analyzing a subset of the measurements in the measurement signal. For example the step of analyzing can comprise analyzing a subset of the measurements within a time window that is then 'slid' across the measurements to provide a new subset of measurements for analysis. The window may be sized according to a typical duration of a sit to stand movement or stand to sit movement. For example, the window may be sized to cover 30 seconds of measurements.

As described above, the first measurement signal may be obtained by a first sensor 4 that indirectly measures the force or pressure exerted on the object, such as an airflow sensor that measures the speed of air entering or exiting an object as force or pressure is applied to the object or an applied force or pressure is reduced.

Figure 6:
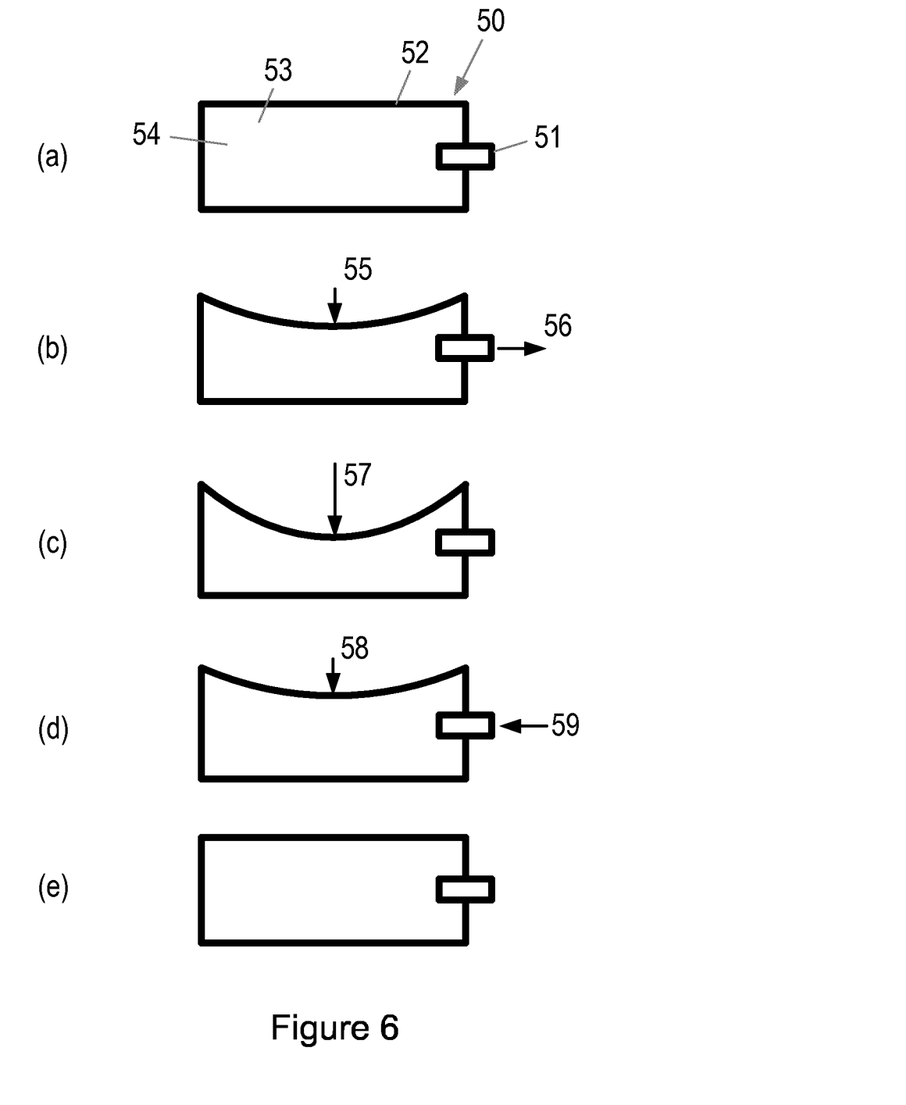
FIG. 6 is a diagram showing how an air flow sensor can be used to measure force or pressure on an object that may be compressed and re-inflated during a stand to sit and subsequent sit to stand movement according to an embodiment.

FIG. 6 shows an object 50 that includes an airflow sensor 51 according to an exemplary embodiment. The object 50 comprises an outer wall 52 that forms an enclosed chamber 53, with the outer wall 52 being generally or completely impermeable to air (i.e. air tight) except for a hole that comprises the air flow sensor 51. The outer wall 52 is made of a material that is deformable, for example, plastic, rubber, leather, fabric, etc. The chamber 53 may include an inner structure 54 that can be partly or completely filled with air. The inner structure 54 may be formed to hold or contain air, and may comprise, for example, sponge or foam with spaces that are filled with air. The inner structure 54 may be configured to deform under pressure or force, and to restore its original shape when the pressure or force is removed. In alternative embodiments, the chamber 53 can be completely filled with air. In this case, the outer wall 52 can be configured to restore its original shape when the pressure or force is removed. In some embodiments, rather than the outer wall 52 being generally or completely impermeable to air, the object 50 may comprising a lining layer that lines the chamber 53, with the lining layer being generally or completely impermeable to air.

The air flow sensor 51 is provided in the outer wall 52, so that air can flow out of the object 50 through the air flow sensor 51 when the object 50 is compressed, and air can flow into the object 50 when a compressing force or pressure acting on the object 50 is reduced or removed (e.g. a subject stands up so that they are no longer sitting on the object 50) and the object 50 returns to its original shape.

In an alternative embodiment to that shown in FIG. 6, the outer wall 52 may be air tight such that no air exits the object 50 when force or pressure is applied to the object 50, but instead air flow may occur between two or more internal portions of object 50. The airflow sensor 51 can be positioned between these internal portions to measure the speed of air flow between the portions. Thus, when a subject sits down on the object 50 air will be pushed from one internal portion through the airflow sensor 51 to another internal portion. The measurement of the air flow speed from the airflow sensor 51 will be an indication of the force or pressure applied to the object 50.

FIG. 6(a) shows the object 50 when a subject is not in contact with the object 50. Thus, the object 50 is in a 'steady state', with no air flow into or out of the object 50.

When a subject starts to apply force or pressure to the object 50 during a sitting motion (e.g. in the direction of arrow 55 in FIG. 6(b)) the object 50 is compressed which causes air to be expelled from object 50 through the airflow sensor 51 in the direction of arrow 56. Once the subject is fully seated, as shown in FIG. 6(c), the object 50 is fully compressed due to the weight of the person in the direction of arrow 57 and there is no further air flow past airflow sensor 51.

When the subject starts to stand up, as shown in FIG. 6(d), the reduction of the downward force or pressure indicated by arrow 58 allows the object 50 to expand (or start to return to its original shape as shown in FIG. 6(a)) which draws air into the object 50 through airflow sensor 51 in the direction of arrow 59. This air flow continues as the force or pressure continues to reduce (i.e. as the subject lifts their whole weight off of the object 50) and the object 50 returns to its original shape, as shown in FIG. 6(e).

Figure 7:
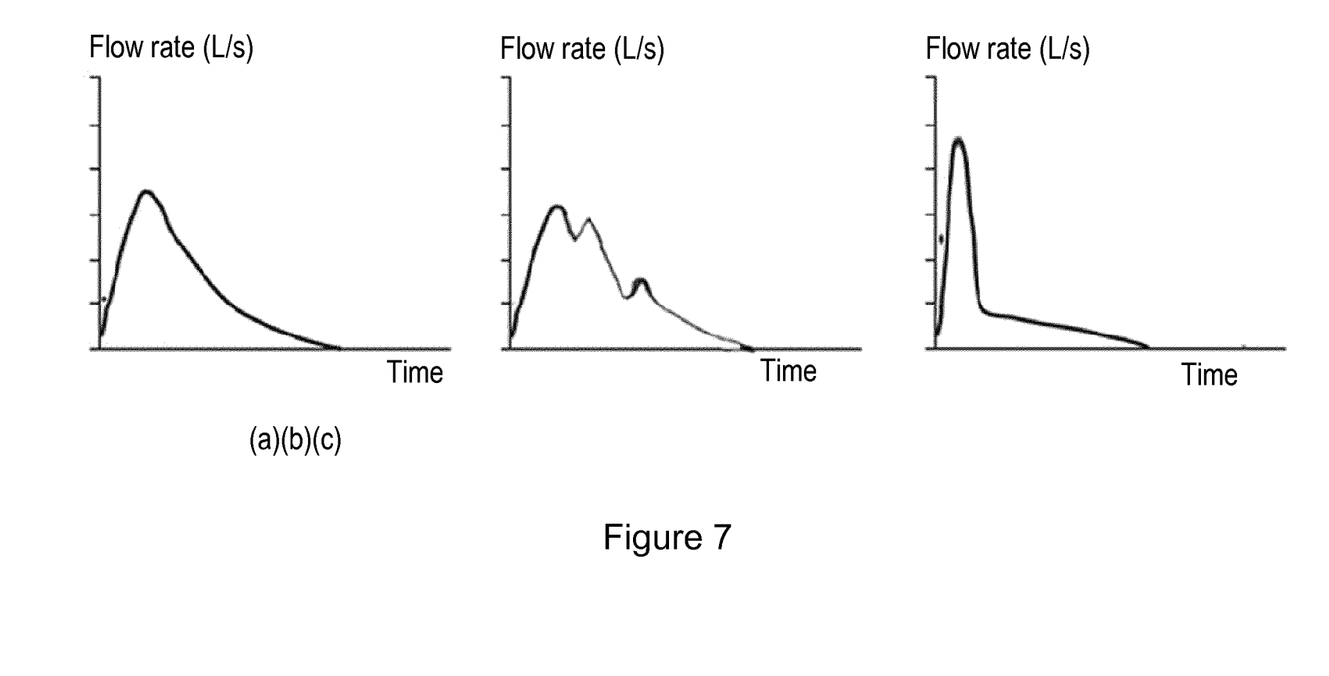
FIG. 7 is a set of graphs showing three profiles of airflow within or from an object during a movement in which the subject sits down on the object.

The graphs in FIG. 7 show measurement signals for air flow rate from an object 50 when a subject sits down on the object 50, i.e. corresponding to FIGS. 6(a)-(c). The three graphs show air flow rate out of an object 50 for three subjects with different levels of physical fitness. FIG. 7(a) shows the air flow rate that might be measured for a subject with a high level of physical fitness. The profile in FIG. 7(a) relatively smoothly increases from a zero flow rate (where the subject first comes into contact with the object 50) to a peak level (where the subject is moving downwards at their quickest rate) to a gradual return to a zero flow rate as the subject finishes the sitting down movement. As with the profile in FIG. 4(a), the profile or curve in FIG. 7(a) is relatively smooth because the subject is able to lower themselves onto the object with a high degree of control without 'slumping' (i.e. just dropping their weight) on to the object 50.

FIG. 7(b) shows the air flow rate profile of a subject with a lower level of physical fitness that is characterized in a jerky, unsteady flow rate as the subject lowers themselves onto the object 50 (similar to FIG. 4(b)).

FIG. 7(c) shows the air flow rate profile of a subject that has a low level of physical fitness. The profile shows a rapid increase in the flow rate to a high peak flow rate, quickly followed by a rapid decrease in the flow rate. This corresponds to the subject 'slumping' onto the object 50.

It will be appreciated that the air flow rate measurement signal can be analyzed to determine the physical fitness as described above for step 34 in the same way as for the direct measurements of force or pressure. Thus, any one or more of the characteristics described above can be derived from the flow rate measurement signal in the same way as described above with respect to the pressure and force curves, and analyzed to determine the measure of the physical fitness.

It will be appreciated that in some embodiments measurement signals from multiple sensors can be used to determine the measure of physical fitness.

As mentioned above, in some embodiments where the first sensor 4 is located on a part of the object on which the subject sits (e.g. a seat portion as shown in FIG. 2), the apparatus 2 can further comprise a second sensor 10 that measures the force or pressure exerted on an arm rest of the object or other object by the subject during the movement in which the subject sits down on the object and/or during the movement in which the subject stands up after sitting on the object. The processing unit 6 can process the first measurement signal from the first sensor 4 and the (second) measurement signal from the second sensor 10 to determine the measure of the physical fitness. In particular the combination of the force or pressure on (e.g.) the seat and the force or pressure on the arm rest allows for the extraction of additional data (i.e. other parameters) on the physical fitness of the subject, for example a measurement of (hand) grip strength.

Figure 8:
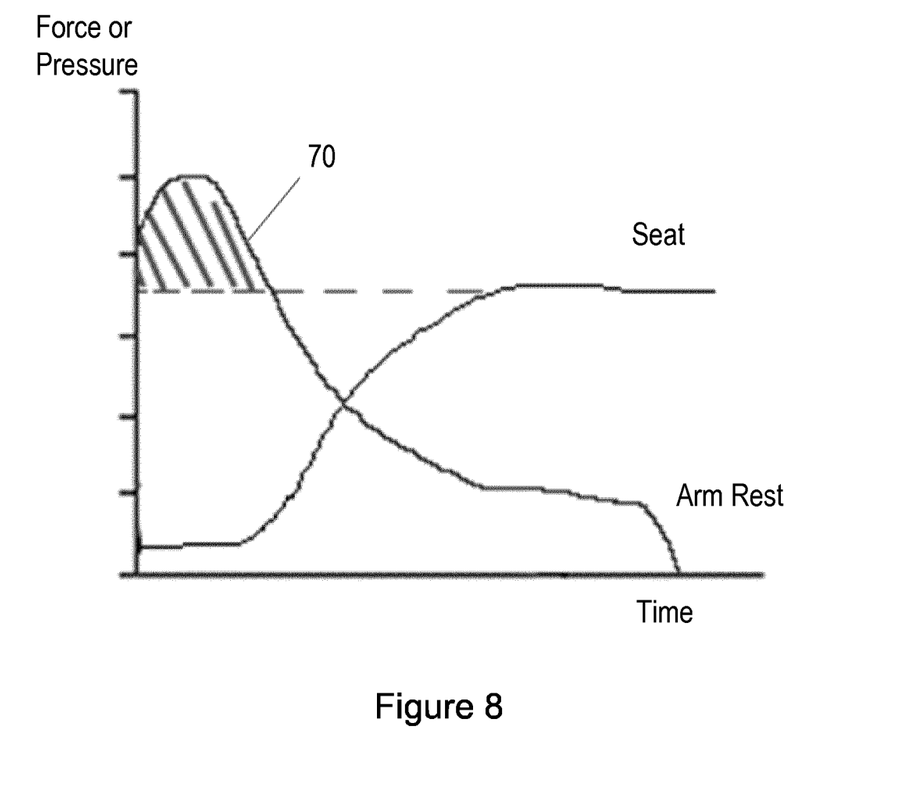
FIG. 8 is a graph of a force/pressure profile on an object and on an arm rest of the object during a movement in which the subject sits down on the object.

The graph in FIG. 8 is a plot of the measurement signal obtained by a first sensor 4 on a seat for a fit subject (e.g. as in FIG. 4(a)) and a plot of the measurement signal 70 obtained by a second sensor 10 located on an arm rest (e.g. associated with the seat or a separate hand rail or walking aid) during a stand to sit movement. It can be seen that the subject applies force or pressure to the arm rest as they start to sit down (but before they make contact with the first sensor 4) and the force or pressure applied to the arm rest generally decreases from an initial peak to zero as the movement progresses.

In some embodiments, the maximum amplitude or maximum magnitude of the second measurement signal during the movement can be determined, and this amplitude or magnitude assessed to provide an indication of the physical fitness of the subject. This indication can be then be combined with indications derived from characteristics of the first measurement signal to determine the overall measure of the physical fitness of the subject. For example a subject with good physical fitness might not need to use the arm rest at all, or just for balance, and therefore the second measurement signal may be constant (i.e. a constant amplitude) during the movement or have a relatively low maximum magnitude. In contrast, a subject with poor physical fitness may need to lean on the arm rest in order to sit down or stand up and therefore exerts a lot of force on the arm rest (including by gripping the arm rest). Therefore a second measurement signal that has a relatively high maximum amplitude can be indicative that the subject has poor physical fitness.

In some embodiments, the force exerted on the arm rest can be approximated as the weight of the subject plus any additional force due to the squeezing or gripping of the arm rest. It will be appreciated that the force exerted on the arm rest may not exactly correspond to the weight of the subject plus any additional squeezing or gripping force since part of the weight of the subject may be supported by the subject's legs. However, during a movement there will also be a component of force required for accelerating the subject upwards (in the case of a sit to stand movement) or decelerating the subject when moving downwards (in the case of a stand to sit movement), and this acceleration or deceleration is assumed to be of a similar magnitude to the part of the weight supported by the legs, which enables the above approximation to be used. The force due to the weight of the subject is constant and will be measured via the first sensor 4 once the subject is fully sitting (in FIG. 8 this is given by the magnitude of the force or pressure on the right hand side of the graph (i.e. after the sit down movement has completed)). Given that the weight force is known, it is possible to determine the force that has been added on top of this due to the gripping force. This is the part of the second measurement signal 70 that is above the maximum force shown in the first measurement signal (i.e. the force above the dashed line, and in the shaded area).

So from the first measurement signal the force related to sitting (i.e. the maximum value of the force in a stable (sitting) situation) is determined. This is denoted $f\_s\_max$. Then $f\_s\_max$ is subtracted from each measurement sample in the second measurement signal 70 (which is denoted $f\_r$). For each sample where $f\_r-f\_s\_max>0$, the values of $f\_r-f\_s\_max$ are summed to calculate the area of shaded part of FIG. 8. Typically, a subject that is fit will not exert much or any additional force on the arm rest, and so the area of the shaded part may be small, but a subject that is not fit (e.g. frail) may squeeze the arm rest significantly, and so the area of the shaded part may be large.

Thus, the apparatus and method described above provide a way to monitor the physical fitness of a subject unobtrusively over time, and thus enable an assessment of the development or deterioration of physical health, such as frailty.

The results of the physical fitness determination can be presented to an end user, for example the subject or a care provider. Information such as key outcomes including a current physical fitness score and a trend analysis for the subject can be provided. Furthermore, the subject or a care provider may be alerted if the subject's physical fitness drops below a certain set threshold for the subject or when there is a significant negative trend detected in the pattern of the physical fitness scores over time.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other processing unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for determining a first measure of physical fitness of a subject, the apparatus comprising a processing unit that is configured to:
   receive a first measurement signal from a first sensor that measures force or pressure exerted on an object by the subject over time, the first measurement signal comprising measurements representing the force or pressure exerted on a part of the object on which the subject sits during a first movement in which the subject sits down on the object and/or during a second movement in which the subject stands up after sitting on the object;
   receive a second measurement signal from a second sensor that measures a second force or pressure exerted on an arm rest that can be used by the subject during the first movement and/or during the second movement, the second measurement signal comprising measurements representing the second force or pressure exerted on the arm rest during the first movement and/or during the second movement;
   analyze the first measurement signal and the second measurement signal to determine the measure of the physical fitness of the subject, wherein the first measure of the physical fitness is a grip strength of the subject;
   determine a force due to weight of the subject, $f\_s\_max$, from the first measurement signal as a maximum value of the first measurement signal following the first movement or as a maximum value of the first measurement signal prior to the second movement;
   subtract the force due to the weight of the subject, $f\_s\_max$, from each measurement in the second measurement signal, $f\_r$, to obtain $f\_r-f\_s\_max$; and
   calculate the grip strength by summing the values of $f\_r-f\_s\_max$ for which $f\_r-f\_s\_max>0$.

2. The apparatus as claimed in claim 1, wherein the processing unit is further configured to analyze one or more characteristics of a profile formed from the first measurement signal to determine a second measure of the physical fitness of the subject.

3. The apparatus as claimed in claim 2, wherein the second measure is based on local maxima and/or local minima in the profile or in a part of the profile.

4. The apparatus as claimed in claim 2, wherein the second measure is based on the derivative with respect to time of the profile.

5. The apparatus as claimed in claim 2, wherein one or more characteristics comprises a maximum magnitude of the first measurement signal.

6. The apparatus as claimed in claim 2, wherein the processing unit is configured to analyze the first measurement signal to determine a start time and an end time of the first movement and/or the second movement, and the one or more characteristics comprises a time between the determined start time and end time.

7. The apparatus as claimed in claim 2, wherein the second measure is based upon a variation of a derivative with respect to time of the profile or part of the profile.

8. The apparatus as claimed in claim 1, wherein the first sensor is a pressure sensor, a force sensor, or an airflow sensor.

9. A method of determining a first measure of physical fitness of a subject, the method comprising:
   receiving a first measurement signal from a first sensor that measures the force or pressure exerted on an object by the subject over time, the first measurement signal comprising measurements representing the force or pressure exerted on a part of the object on which the subject sits during a first movement in which the subject sits down on the object and/or during a second movement in which the subject stands up after sitting on the object;
   receiving a second measurement signal from a second sensor that measures a second force or pressure exerted on an arm rest that can be used by the subject during the first movement and/or during the second movement, the second measurement signal comprising measurements representing the force or pressure exerted on the arm rest during the first movement and/or during the second movement;
   analyzing the first and second measurement signal to determine the measure of the physical fitness of the subject; wherein the first measure of the physical fitness is grip strength of the subject;
   determining a force due to the weight of the subject, f_s_max, from the first measurement signal as a maximum value of the first measurement signal following the first movement or as a maximum value of the first measurement signal prior to the second movement;
   subtracting the force due to the weight of the subject, f_s_max, from each measurement in the second measurement signal, f_r, to obtain f_r−f_s_max; and
   calculating the grip strength by summing the values of f_r−f_s_max for which f_r−f_s_max>0.

10. The method as claimed in claim 9, further comprising:
    analyzing one or more characteristics of a profile formed from the first measurement signal to determine a second measure of the physical fitness of the subject.

11. The method as claimed in claim 9, wherein the one or more characteristics comprises any one or more of:
    a measure based on local maxima and/or local minima in the profile or in a part of the profile;
    a measure based on the derivative with respect to time of the profile;
    a maximum magnitude of the first measurement signal;
    a time between a start time and end time of the first movement and/or the second movement; and
    a measure of a variation of a derivative with respect to time of the profile or part of the profile.

12. A non-transitory computer readable medium having computer readable code embodied therein, the computer readable code being configured such that, on execution by a suitable computer or processor, the computer or processor is caused to perform a method of determining a first measure of physical fitness of a subject, the non-transitory computer readium medium comprising:
    instructions for receiving a first measurement signal from a first sensor that measures the force or pressure exerted on an object by the subject over time, the first measurement signal comprising measurements representing the force or pressure exerted on a part of the object on which the subject sits during a first movement in which the subject sits down on the object and/or during a second movement in which the subject stands up after sitting on the object;
    instructions for receiving a second measurement signal from a second sensor that measures a second force or pressure exerted on an arm rest that can be used by the subject during the first movement and/or during the second movement, the second measurement signal comprising measurements representing the force or pressure exerted on the arm rest during the first movement and/or during the second movement;
    instructions for analyzing the first and second measurement signal to determine the measure of the physical fitness of the subject; wherein the first measure of the physical fitness is the grip strength of the subject;
    instructions for determining a force due to the weight of the subject, f_s_max, from the first measurement signal as a maximum value of the first measurement signal following the first movement or as a maximum value of the first measurement signal prior to the second movement;
    instructions for subtracting the force due to the weight of the subject, f_s_max, from each measurement in the second measurement signal, f_r, to obtain f_r−f_s_max; and
    instructions for calculating the grip strength by summing the values of f_r−f_s_max for which f_r−f_s_max>0.

* * * * *